(12) United States Patent
Fitzpatrick et al.

(10) Patent No.: US 7,780,622 B2
(45) Date of Patent: Aug. 24, 2010

(54) ARTIFICIAL BLOOD VESSEL

(75) Inventors: Charles Fitzpatrick, Renfrewshire (GB); Tadanori Okubo, Glasgow (GB)

(73) Assignees: Vascutek Limited, Inchinnan (GB); Terumo Corporation, Tokyo (JP)

( * ) Notice: Subject to any disclaimer, the term of this patent is extended or adjusted under 35 U.S.C. 154(b) by 0 days.

(21) Appl. No.: 11/792,498

(22) PCT Filed: Feb. 14, 2005

(86) PCT No.: PCT/GB2005/000521

§ 371 (c)(1),
(2), (4) Date: Jun. 6, 2007

(87) PCT Pub. No.: WO2006/085044

PCT Pub. Date: Aug. 17, 2006

(65) Prior Publication Data

US 2008/0097592 A1 Apr. 24, 2008

(51) Int. Cl.
*A61M 5/00* (2006.01)
*A61F 2/06* (2006.01)

(52) U.S. Cl. .......................... 604/8; 623/1.15; 623/1.3; 623/1.32; 623/1.34; 623/1.44

(58) Field of Classification Search ................ 623/1.13, 623/1.3, 1.34, 1.44, 1.49, 23.64, 903, FOR. 108; 64/8, 6.16, 174, 175; 606/108, 175, 151; 600/36; 138/137, 120, 141, 149
See application file for complete search history.

(56) References Cited

U.S. PATENT DOCUMENTS

| | | | | |
|---|---|---|---|---|
| 3,496,939 A * | 2/1970 | Odiaga et al. | | 606/154 |
| 3,919,724 A | 11/1975 | Sanders et al. | | 3/36 |
| 4,202,349 A * | 5/1980 | Jones | | 600/502 |
| 4,619,641 A * | 10/1986 | Schanzer | | 604/8 |
| 4,772,276 A * | 9/1988 | Wiita et al. | | 604/533 |
| 4,883,453 A * | 11/1989 | Berry et al. | | 600/36 |
| 5,472,746 A * | 12/1995 | Miyajima et al. | | 427/468 |
| 5,533,985 A * | 7/1996 | Wang | | 604/264 |
| 5,628,782 A * | 5/1997 | Myers et al. | | 623/2.25 |
| 5,800,514 A * | 9/1998 | Nunez et al. | | 623/1.51 |
| 5,823,231 A * | 10/1998 | Kawasaki | | 138/109 |
| 5,866,217 A * | 2/1999 | Stenoien et al. | | 623/1.44 |

(Continued)

FOREIGN PATENT DOCUMENTS

EP 0 808 637 11/1997

(Continued)

*Primary Examiner*—Leslie R Deak
*Assistant Examiner*—Adam Marcetich
(74) *Attorney, Agent, or Firm*—Drinker Biddle & Reath LLP

(57) ABSTRACT

There is described an artificial blood vessel for use in a region of a living body which needs to be repeatedly pierced with a needle. The artificial blood vessel includes a main section having a vessel wall which includes a laminated assembly comprising an inner layer, an outer layer, and an intermediate layer positioned therebetween, and a pair of anastomotic sections disposed on the respective opposite ends of the main section. Each of the anastomotic sections has an intermediate layer thinner than the intermediate layer of the main section or is free of an intermediate layer, so that the anastomotic section as a vessel wall thinner than the main section.

15 Claims, 7 Drawing Sheets

U.S. PATENT DOCUMENTS

| | | | |
|---|---|---|---|
| 5,918,643 A * | 7/1999 | Roloff et al. | 138/137 |
| 5,989,287 A * | 11/1999 | Yang et al. | 623/1.36 |
| 6,007,478 A * | 12/1999 | Siess et al. | 600/16 |
| 6,146,414 A * | 11/2000 | Gelman | 623/1.23 |
| 6,261,257 B1 * | 7/2001 | Uflacker et al. | 604/9 |
| 6,319,279 B1 * | 11/2001 | Shannon et al. | 623/1.44 |
| 6,585,762 B1 * | 7/2003 | Stanish | 623/1.3 |
| 6,663,614 B1 * | 12/2003 | Carter | 604/525 |
| 6,821,295 B1 * | 11/2004 | Farrar | 623/1.31 |
| 2002/0049403 A1 * | 4/2002 | Alanis | 604/8 |
| 2003/0100859 A1 * | 5/2003 | Henderson et al. | 604/8 |
| 2004/0064130 A1 * | 4/2004 | Carter | 604/523 |
| 2004/0176791 A1 * | 9/2004 | Lim et al. | 606/194 |
| 2004/0193242 A1 * | 9/2004 | Lentz et al. | 623/1.4 |
| 2004/0215337 A1 * | 10/2004 | Hain et al. | 623/1.44 |
| 2006/0111733 A1 * | 5/2006 | Shriver | 606/153 |

FOREIGN PATENT DOCUMENTS

| | | |
|---|---|---|
| WO | WO 94/13224 | 6/1994 |
| WO | WO 99/44487 | 9/1999 |
| WO | WO 01/23023 | 4/2001 |
| WO | WO 01/28456 | 4/2001 |
| WO | WO 02/102277 | 12/2002 |
| WO | WO 03/045282 | 6/2003 |
| WO | WO 2004/096307 | 11/2004 |

* cited by examiner

ARTIFICIAL BLOOD VESSEL

BACKGROUND OF THE INVENTION

The present invention relates to an artificial blood vessel for use in a region of a living body, which region needs to be repeatedly pierced with a needle.

Medical operations for replacing or bypassing a blood vessel in a living body with an artificial blood vessel, or artificial blood vessel grafting, are practiced in the medical field.

Some artificial blood vessels implanted in such operations are used in hemodialysis (dialysis treatment), for example, a blood passageway known as an arterial-venous (A-V) shunt interconnecting an artery and a vein, which is intended to be repeatedly pierced with a needle. One such artificial blood vessel (artificial prosthesis) is disclosed in British Patent No. 1506432, for example. The disclosed artificial blood vessel has a vessel wall comprising a single layer of expanded polytetrafluoroethylene (ePTFE).

The artificial blood vessel of such a structure has the disadvantage that, as it is repeatedly pierced with a needle, a number of holes are opened in the vessel wall, allowing the blood to leak therefrom.

SUMMARY OF THE INVENTION

It is an object of the present invention to provide an artificial blood vessel which is reliably effective to prevent blood from leaking out even if it is repeatedly pierced with a needle, and which can easily be joined to an existing blood vessel in a living body.

The above object can be achieved by an artificial blood vessel comprising a main section having a vessel wall which includes a laminated assembly comprising an inner layer, an outer layer and an intermediate layer positioned therebetween, and an anastomotic section disposed on each or one of opposite ends of the main section, wherein the anastomotic section has an intermediate layer thinner than the intermediate layer of the main section so that the anastomotic section has a vessel wall thinner than the main section. Such an artificial blood vessel can be used in a region of a living body which needs to be repeatedly pierced with a needle without significant leakage of blood.

In the anastomotic section, the minimum thickness of the intermediate layer is limited only by the amount needed to bond the inner and outer layers together.

In one embodiment, the intermediate layer of the anastomotic section has a thickness in the range from 10 to 90% of the thickness of the intermediate layer of the main section.

In a further embodiment, the intermediate layer of the anastomotic section has a thickness in the range of 40 to 60% of the thickness of the intermediate layer of the main section.

An exemplary cross-sectional thickness for the intermediate layer in the main section is 0.05 to 1.0 mm, for example 0.1 to 0.6 mm. An exemplary cross-sectional thickness for the intermediate layer in the anasomotic section is 0.005 mm to 0.9 mm, preferably is 0.005 to 0.6 mm.

An exemplary cross-sectional thickness for the inner layer is 0.05 to 1.0 mm, for example 0.1 to 0.6 mm.

An exemplary cross-sectional thickness for the outer layer is 0.02 to 0.3 mm, for example 0.05 to 0.2 mm.

The anastomotic section can have an outside diameter smaller than the outside diameter of the main section.

In one embodiment, the intermediate layer consists substantially of an elastic material, for example thermoplastic elastomer. Suitable thermoplastic elastomers include a styrene elastomer, a polyolefin elastomer, a polyvinyl chloride elastomer, a polyurethane elastomer, a polyester elastomer, a polyamide elastomer, a polybutadiene elastomer, a transpolyisoprene elastomer, a fluororubber elastomer, a chlorinated polyethyelene elastomer or the like.

Of the above self-closable elastomeric materials, styrene thermoplastic elastomers are preferred. In particular, a styrene-ethylene-butylene-styrene block copolymer (SEBS), a styrene-ethylene-propylene-styrene block copolymer (SEPS), and hydrogenated styrene-isoprene-butadiene block copolymer (SEEPS) are preferred.

In one embodiment the inner layer and/or the outer layer consists substantially of a fluoroplastic material. Suitable fluoroplastic materials include expanded polytetrafluoroethylene (ePTFE), tetrafluoroethylene-perfluoroalkyl vinyl ether copolymer, tetrafluoroethylene-hexafluoropolypropylene copolymer, tetrafluoroethylene ethylene copolymer or the like.

The inner layer made of such a material is biocompatible to allow the blood to flow smoothly through the artificial blood vessel and also to allow the tissue around the artificial blood vessel to heal well.

The inner layer should preferably have inherent antithrombogenic properties. If the inner layer has no or little antithrombogenicity, then a layer of antithrombotic material may be disposed on the inner surface of the inner layer, or the inner layer itself may carry an antithrombotic material. The antithrombotic material is not limited to any particular material, but may be heparin, urokinase, aspirin, fibrin, or a prostacyclin-based material.

It is not necessary for both the inner layer and the outer layer to be made of a material including fluoroplastic as the majority component, but in certain embodiments either one of the inner layer and the outer layer may be made of a material including fluoroplastics as the majority component.

The artificial blood vessel may further comprise markers for distinguishing the main section and the anastomotic section from each other.

The markers may be disposed respectively on the main section and the anastomotic section, and can be different from each other.

The markers may be used when the artificial blood vessel is embedded into a living body.

Alternatively or additionally, the markers may be used after the artificial blood vessel is embedded into a living body.

The artificial blood vessel may be entirely in the shape of an I (i.e. is rod-shaped) in its natural state.

The artificial blood vessel may be entirely in the shape of a U in its natural state.

The artificial blood vessel may include a U-shaped curved portion disposed on the main section.

In one embodiment the intermediate layer of the main section has a portion having a thickness different from the thickness of another portion thereof.

The main section may have an essentially elliptical or circular transverse cross-sectional shape.

With the above arrangement according to the present invention, since the thickness of the vessel wall of the anastomotic section is smaller than the thickness of the vessel wall of the main section, the artificial blood vessel can easily be anastomosed or joined to an existing blood vessel in the living body.

If the artificial blood vessel includes the markers described above, then the markers can, for example, allow an easy confirmation of the extent of the main section of the artificial blood vessel, i.e. a region of the artificial blood vessel which is intended to be pierced with a needle. When the artificial blood vessel is implanted into the living body, the artificial blood vessel can reliably be placed into a position which is suitable for being pierced with the needle.

The above and other objects, features, and advantages of the present invention will become apparent from the following description when taken in conjunction with the accompanying drawings, which illustrate preferred embodiments of the present invention by way of example.

DESCRIPTION OF THE PREFERRED EMBODIMENTS

First Embodiment

Figure 1:
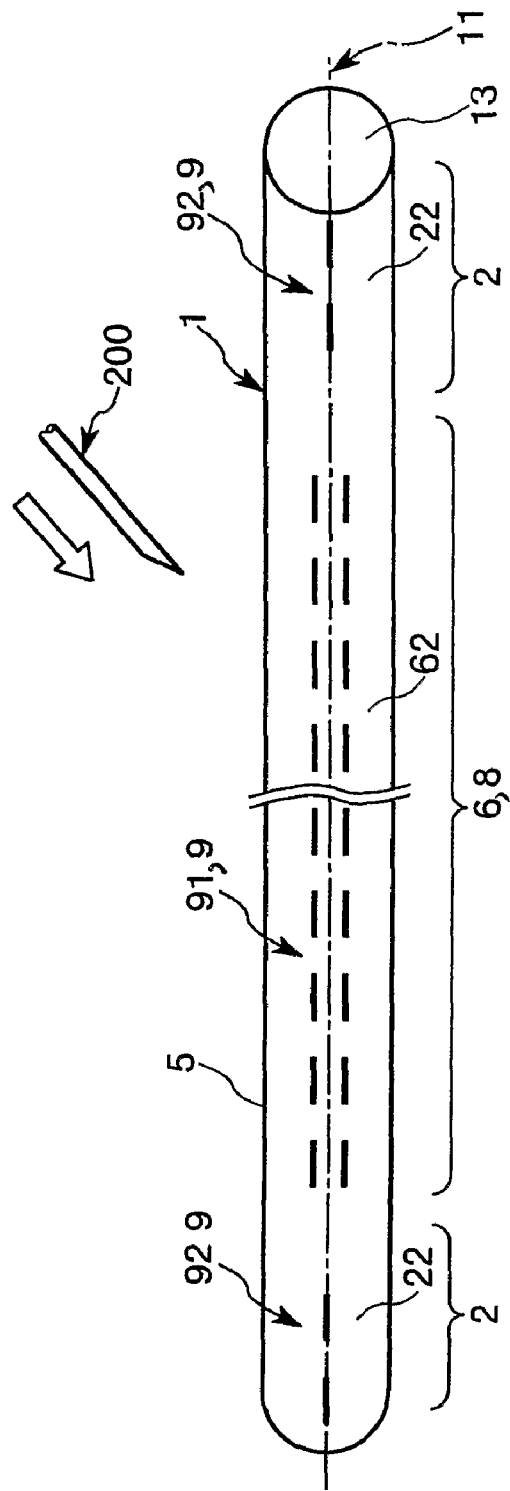
FIG. 1 is a perspective view of an artificial blood vessel according to a first embodiment of the present invention.
Figure 2:
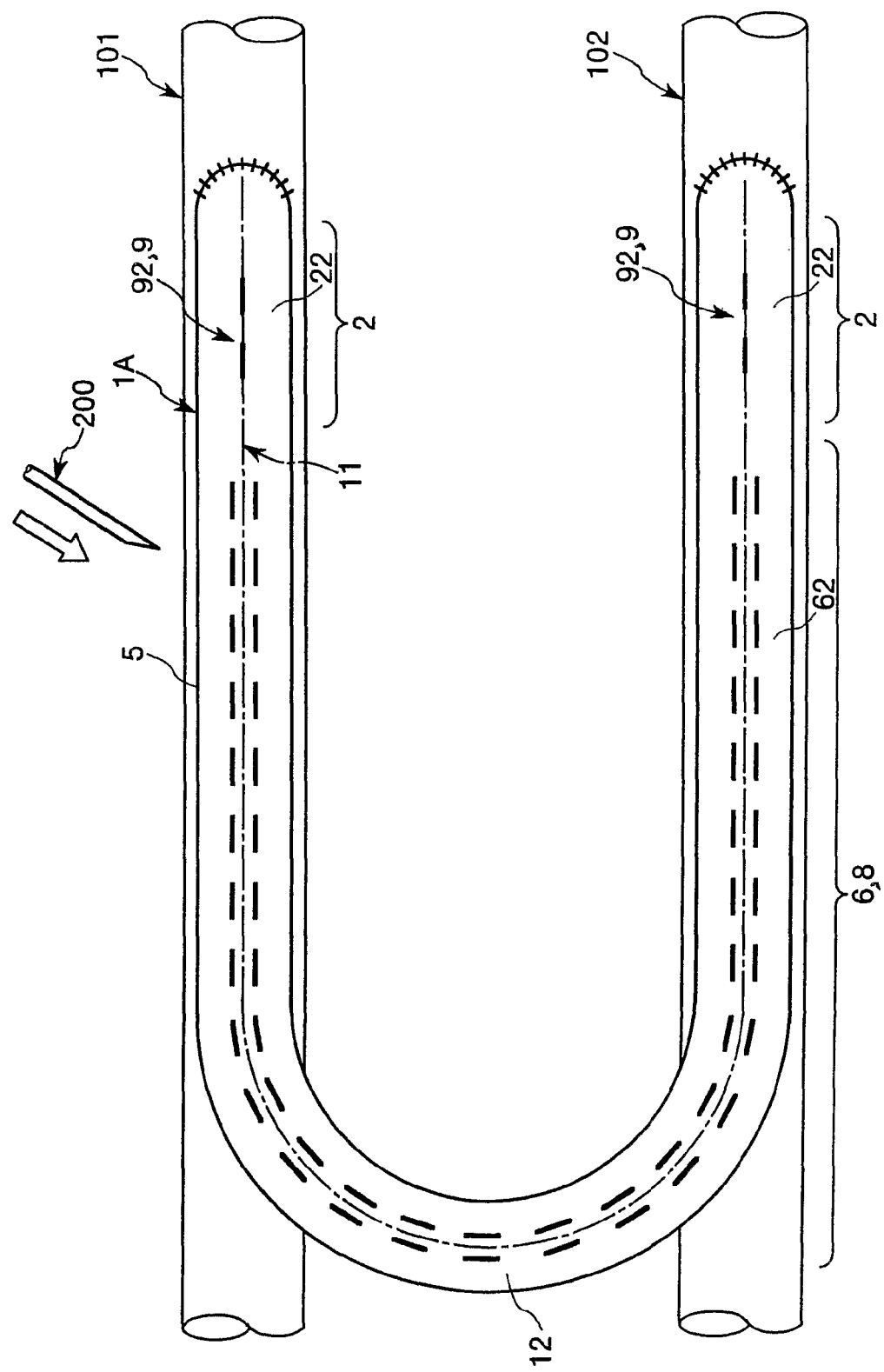
FIG. 2 is a perspective view of the artificial blood vessel shown in FIG. 1, which is implanted between two native blood vessels in a living body.
Figure 3:
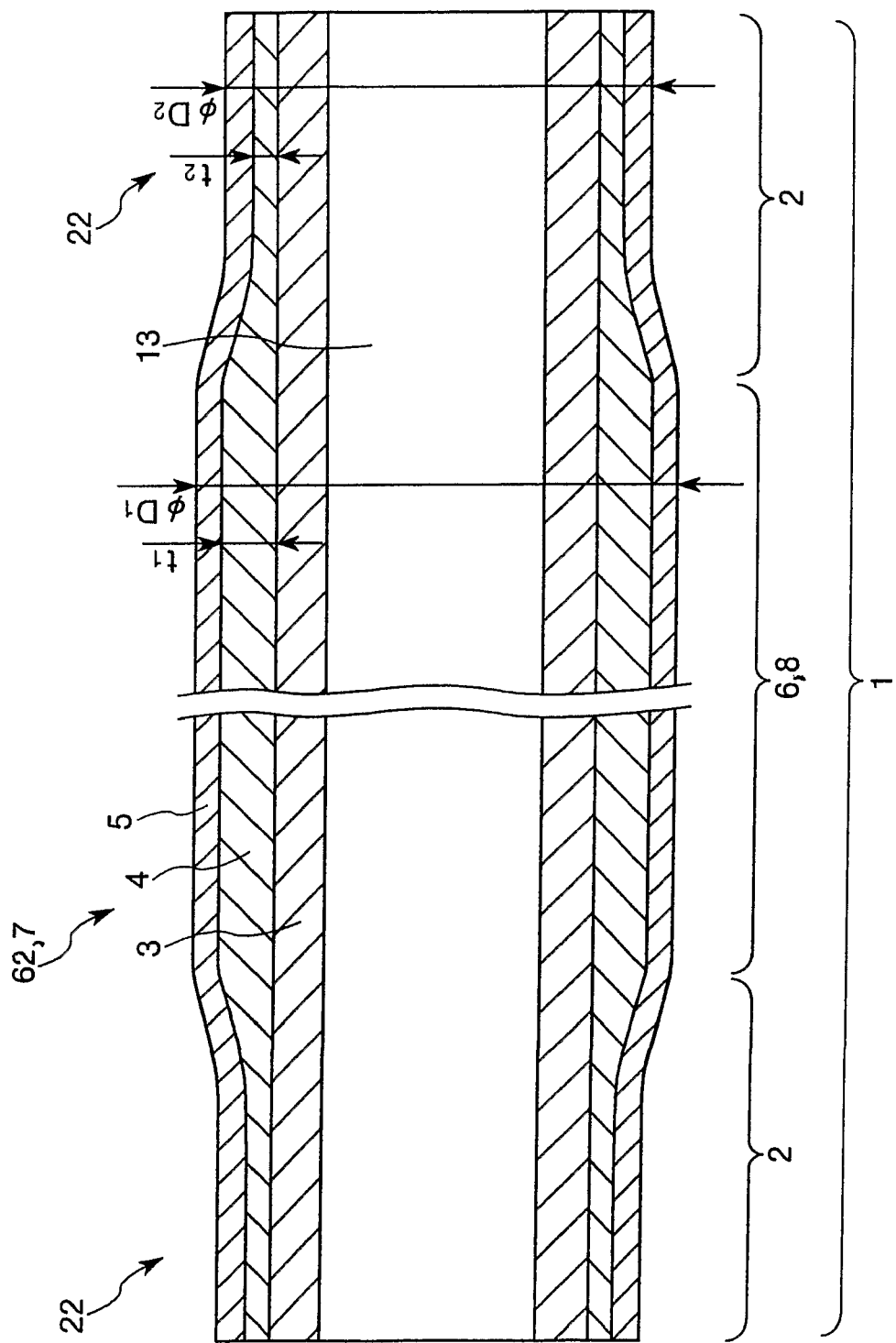
FIG. 3 is an enlarged fragmentary longitudinal cross-sectional view of the artificial blood vessel shown in FIG. 1.

FIGS. 1 through 3 show an artificial blood vessel according to a first embodiment of the present invention.

FIG. 1 is a perspective view of an artificial blood vessel according to a first embodiment of the present invention. FIG. 2 is a perspective view of the artificial blood vessel shown in FIG. 1, which is implanted between two existing blood vessels in a living body. FIG. 3 is an enlarged fragmentary longitudinal cross-sectional view of the artificial blood vessel shown in FIG. 1. Terms related to vertical directions, such as "upper" and "lower", are referred to with respect to FIG. 3. In FIG. 3, the vessel wall of the artificial blood vessel has its thickness shown as exaggerated compared with the outside diameter of the artificial blood vessel.

As shown in FIG. 2, an artificial blood vessel 1 is implanted in a living body between an existing blood vessel (artery) 101 and another existing blood vessel (vein) 102. The artificial blood vessel 1 can be used as a shunt in a body region that needs to be repeatedly pierced with a needle 200 for hemodialysis (dialysis treatment), for example.

As shown in FIG. 1, the artificial blood vessel 1 is flexible and is entirely in the shape of an I (rod-shaped) in its natural state. When the artificial blood vessel 1 is to be embedded in a living body, i.e. is to be placed in the living body to interconnect the living blood vessels 101, 102 (see FIG. 2), the artificial blood vessel 1 can be easily deformed to the desired shape. The artificial blood vessel 1 is not limited to any particular deformed shape, but may be partially curved in its main section 6 or may be a wavy shape in its entirety, for example.

The artificial blood vessel 1 has a main section 6 and a pair of anastomotic sections 2 on the respective ends of the main section 6 for being anastomosed to living blood vessels 101, 102, respectively. These sections of the artificial blood vessel 1 will be described in detail below.

The main section 6 has a circular transverse cross-sectional shape. The main section 6 has a vessel wall 62 comprising a three-layer laminated assembly 7.

As shown in FIG. 3, the laminated assembly 7 comprises an inner layer 3, an outer layer 5, and an intermediate layer 4 positioned therebetween. These layers are disposed concentrically to each other.

The intermediate layer 4 is preferably, but not necessarily, made of any of various elastic materials. An elastic material, which is self-closable after it is punctured is especially preferable. Self-closable elastic materials may be various thermoplastic elastomers including a styrene elastomer, a polyolefin elastomer, a polyvinyl chloride elastomer, a polyurethane elastomer, a polyester elastomer, a polyamide elastomer, a polybutadiene elastomer, a transpolyisoprene elastomer, a fluororubber elastomer, a chlorinated polyethyelene elastomer, etc. The intermediate layer 4 may be made of at least one of the above elastomeric materials as a chief material.

Of the above self-closable elastomeric materials, styrene thermoplastic elastomers are preferable. In particular, a styrene-ethylene-butylene-styrene block copolymer (SEBS), a styrene-ethylene-propylene-styrene block copolymer (SEPS), and hydrogenated styrene-isoprene-butadiene block copolymer (SEEPS) are preferable.

When the needle 200 is removed from the intermediate layer 4, the hole that has been formed in the intermediate layer 4, i.e. the vessel wall 62, by the piercing with the needle 200, is reliably closed off and sealed due to the elasticity of the intermediate layer 4 which is made of at least one of the above self-closable elastomeric materials.

The intermediate layer 4 in the main section 6 has a thickness $t_1$ (see FIG. 3), which is not limited to any value, but may be in the range from 0.1 to 0.6 mm, for example.

The inner layer 3 is not limited to any materials, but may be made of a material including, as a chief component, a fluoroplastic material such as expanded polytetrafluoroethylene (ePTFE), tetrafluoroethylene-perfluoroalkyl vinyl ether copolymer, tetrafluoroethylene-hexafluoropolypropylene copolymer, or tetrafluoroethylene ethylene copolymer.

The inner layer 3 made of such a material is biocompatible to allow the blood to flow smoothly through the artificial blood vessel 1, i.e. a blood passageway 13 defined therein, and also to allow the tissue around the artificial blood vessel 1 to be healed well.

The inner layer 3 should preferably have antithrombogenicity by itself. If the inner layer 3 has no or little antithrombogenicity, then a layer made of antithrombotic material may be disposed on the inner surface of the inner layer 3, or the inner layer 3 itself may carry an antithrombotic material. The antithrombotic material is not limited to any particular material, but may be heparin, urokinase, aspirin, fibrin, or a prostacyclin-based material.

The inner layer 3 has a thickness which is not limited to any value, but may be in the range from 0.1 to 0.6 mm, for example.

The outer layer 5 is not limited to any materials, but may be made of the material as the inner layer 3. The outer layer 5 made of such a material is biocompatible, and allows the tissue around the artificial blood vessel 1 to be healed well.

The outer layer 5 has a thickness which is not limited to any value, but may be in the range from 0.05 to 0.2 mm, for example.

As shown in FIGS. 1 and 3, each of the anastomotic sections 2 is integrally joined to one of the opposite ends of the main section 6. Each of the anastomotic sections 2 has a vessel wall 22 made up of an inner layer 3, an outer layer 5, and an intermediate layer 4 as with the vessel wall 62 of the main section 6.

As shown in FIG. 3, the intermediate layer 4 of each of the anastomotic sections 2 is thinner than the intermediate layer 4 of the main section 6. Therefore, the vessel wall 22 of each of the anastomotic sections 2 is thinner than the vessel wall 62 of the main section 6.

The ratio of the thickness $t_2$ (see FIG. 3) of the intermediate layer 4 of each of the anastomotic sections 2 to the thickness $t_1$ of the intermediate layer 4 of the main section 6 is not limited to any particular value. The thickness $t_2$ of the intermediate layer 4 of each of the anastomotic sections 2 should preferably be 10 to 90%, and more preferably be 40 to 60%, of the thickness $t_1$ of the intermediate layer 4 of the main section 6. The thickness of $t_2$ must be greater than zero to ensure bonding of the layers.

Since the main section 6 of the artificial blood vessel 1 includes an intermediate layer 4 which is thicker than the intermediate layer 4 of each of the anastomotic sections 2, the main section 6 may be used as a region (hereinafter referred to as "puncture region 8") to be pierced with the needle 200. Even when the main section 6, i.e. the puncture region 8, is repeatedly pierced with the needle 200, holes formed in the vessel wall 62 by the needle 200 are closed by the intermediate layer 4, reliably preventing the blood from leaking out of the holes.

Since the vessel wall 22 of each of the anastomotic sections 2 is relatively thin, the anastomotic sections 2 can easily be anastomosed or sutured to the living blood vessels 101, 102.

As shown in FIG. 3, the intermediate layer 4 is present with a constant thickness in the whole circumference of the main section 6, making the artificial blood vessel 1 symmetrical around the central axis 11 thereof, i.e. making the artificial blood vessel 1 universally directional around the central axis 11. Accordingly, the artificial blood vessel 1 can be handled easily when it is embedded in the living body.

As shown in FIG. 3, the outside diameter $\phi D_2$ of each of the anastomotic sections 2 should preferably be smaller than the outside diameter $\phi D_1$ of the main section 6. Specifically, the difference between the outside diameter $\phi D_2$ and the outside diameter $\phi D_1$ should preferably be continuously varied to make the main section 6 blend smoothly into the anastomotic sections 2. If the difference between the outside diameter $\phi D_2$ and the outside diameter $\phi D_1$ is not continuously varied, i.e., if there is an abrupt step between the main section 6 and each of the anastomotic sections 2, then the artificial blood vessel 1 would tend to be brought into frictional contact with the subcutaneous tissue or tend to become bent or kinked when implanted in the living body.

The inside diameter of the artificial blood vessel 1 may be reduced in only one of the anastomotic sections 2. If the inside diameter of only one of the anastomotic sections 2 is reduced, then the inside diameter of the main section 6 joined thereto should preferably continuously increased in the direction away from the anastomotic section 2 over a predetermined distance, so that the inner wall surface of the main section 6 smoothly blends into the inner wall surface of the anastomotic section 2 without any abrupt steps. The predetermined distance over which the inside diameter of the main section 6 is continuously increased may extend partly or fully along the main section 6.

The artificial blood vessel 1 should preferably have markers 9 for visually distinguishing the main section 6 and the anastomotic sections 2 from each other. After the artificial blood vessel 1 is embedded in the living body, the markers 9 give a visual indication of the extent of the puncture region 8 of the embedded artificial blood vessel 1.

As shown in FIG. 1, the markers 9 include a main section marker 91 disposed on the main section 6, i.e. on the outer layer 5 thereof, and anastomotic section markers 92 disposed on the anastomotic sections 2, i.e. the outer layers 5 thereof.

In the embodiment illustrated, the main section marker 91 comprises two broken lines extending along the central axis 11 of the artificial blood vessel 1. Each of the anastomotic section markers 92 comprises a single broken line extending along the central axis 11.

Since the main section marker 91 and the anastomotic section markers 92 have different structures or features, they allow the main section 6 and the anastomotic sections 2 to be reliably distinguished from each other and hence to allow the puncture region 8 to be reliably recognized.

The markers 9 are not limited to being formed on both the main section 6 and the anastomotic sections 2, but may be provided on either the main section 6 or on the anastomotic sections 2.

With the arrangement shown in FIG. 3, the thickness of the outer layer 5 is essentially constant throughout the main section 6 and the anastomotic sections 2. However, the outer layer 5 may be thicker in the main section 6 than in the anastomotic sections 2.

Second Embodiment

Figure 4:
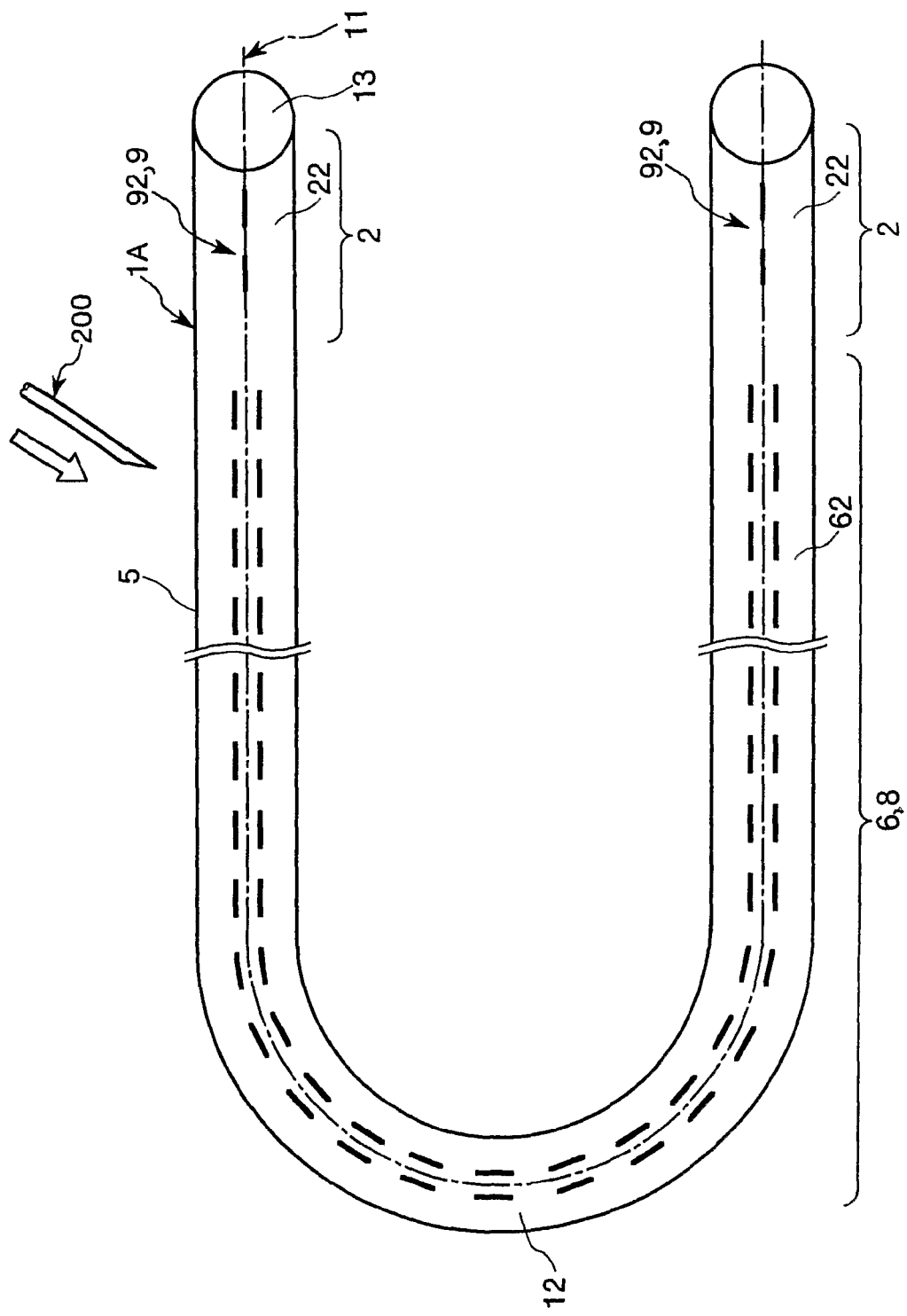
FIG. 4 is a perspective view of an artificial blood vessel according to a second embodiment of the present invention.

FIG. 4 shows in perspective view an artificial blood vessel according to a second embodiment of the present invention.

Those features of the artificial blood vessel according to the second embodiment which are different to the artificial blood vessel according to the first embodiment will mainly be described below, and other features common to both the first and second embodiments will not be described below.

As shown in FIG. 4, an artificial blood vessel 1A according to the second embodiment is entirely in the shape of a U in its natural state, and provides a long puncture region 8. This long puncture region 8 has a large surface area to provide more locations that can be pierced with the needle 200. The artificial blood vessel 1A thus constructed is useful in dialysis treatment.

The artificial blood vessel 1A includes a U-shaped curved portion 12 positioned on the main section 6. Therefore, the artificial blood vessel 1A has a reduced overall size and can easily be embedded in the living body.

Third Embodiment

Figure 5:
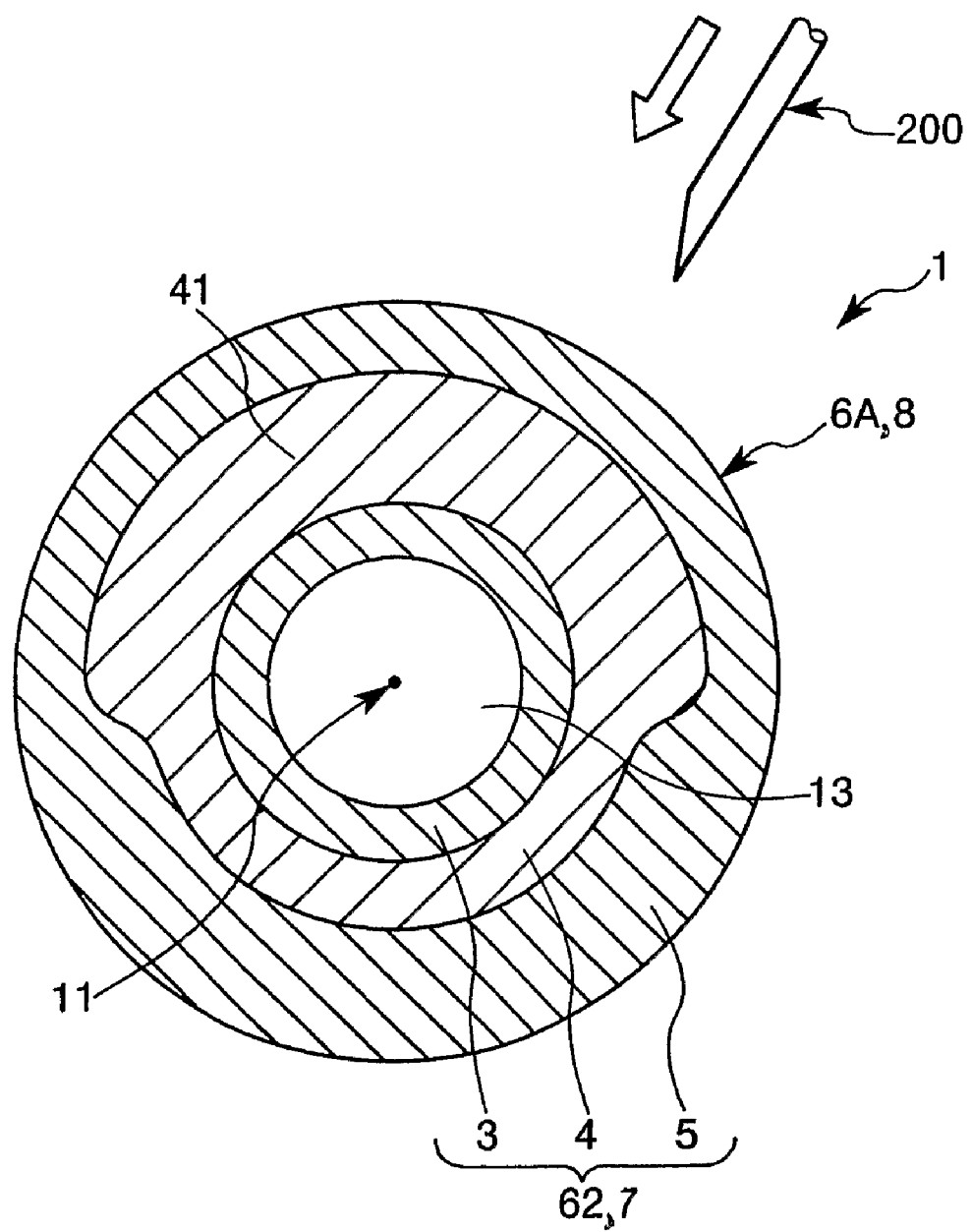
FIG. 5 is a transverse cross-sectional view of a main section of an artificial blood vessel according to a third embodiment of the present invention.

FIG. 5 shows in transverse cross-section the main section of an artificial blood vessel according to a third embodiment of the present invention. Terms related to vertical directions, such as "upper" and "lower", refer to the orientation of the vessel shown in FIG. 5. In FIG. 5, the vessel wall of the artificial blood vessel has its thickness shown in exaggerated form, as compared with the outside diameter of the artificial blood vessel.

Those features of the artificial blood vessel according to the third embodiment which are different from the artificial blood vessel according to the above embodiments will mainly be described below, and other common features will not be described below.

As shown in FIG. 5, the intermediate layer 4 of the main section 6A has two portions of different thicknesses. Specifically, in the main section 6A of the artificial blood vessel 1, the thickness of a circumferential portion of the intermediate layer 4, i.e. the thickness of the upper portion of the intermediate layer 4 (which will be hereinafter referred to as "upper intermediate layer 41") is greater than the thickness of the lower portion of the intermediate layer 4.

If the artificial blood vessel 1 is pierced with the needle 200 in a predetermined direction, i.e., from an upper side in FIG. 5, then the artificial blood vessel 1 can be placed in the living body such that the upper intermediate layer 41 is positioned in alignment with that direction. In the main section 6A, the intermediate layer 4 does not need to have a constant circumferential thickness, in contrast to the first embodiment.

The thickness of the lower portion of the intermediate layer 4 of the main section 6A may be equal to the thickness of the intermediate layer 4 of each of the anastomotic sections 2, or may be of a value intermediate between the thickness of the upper intermediate layer 41 and the thickness of the intermediate layer 4 of each of the anastomotic sections 2.

Fourth Embodiment

Figure 6:
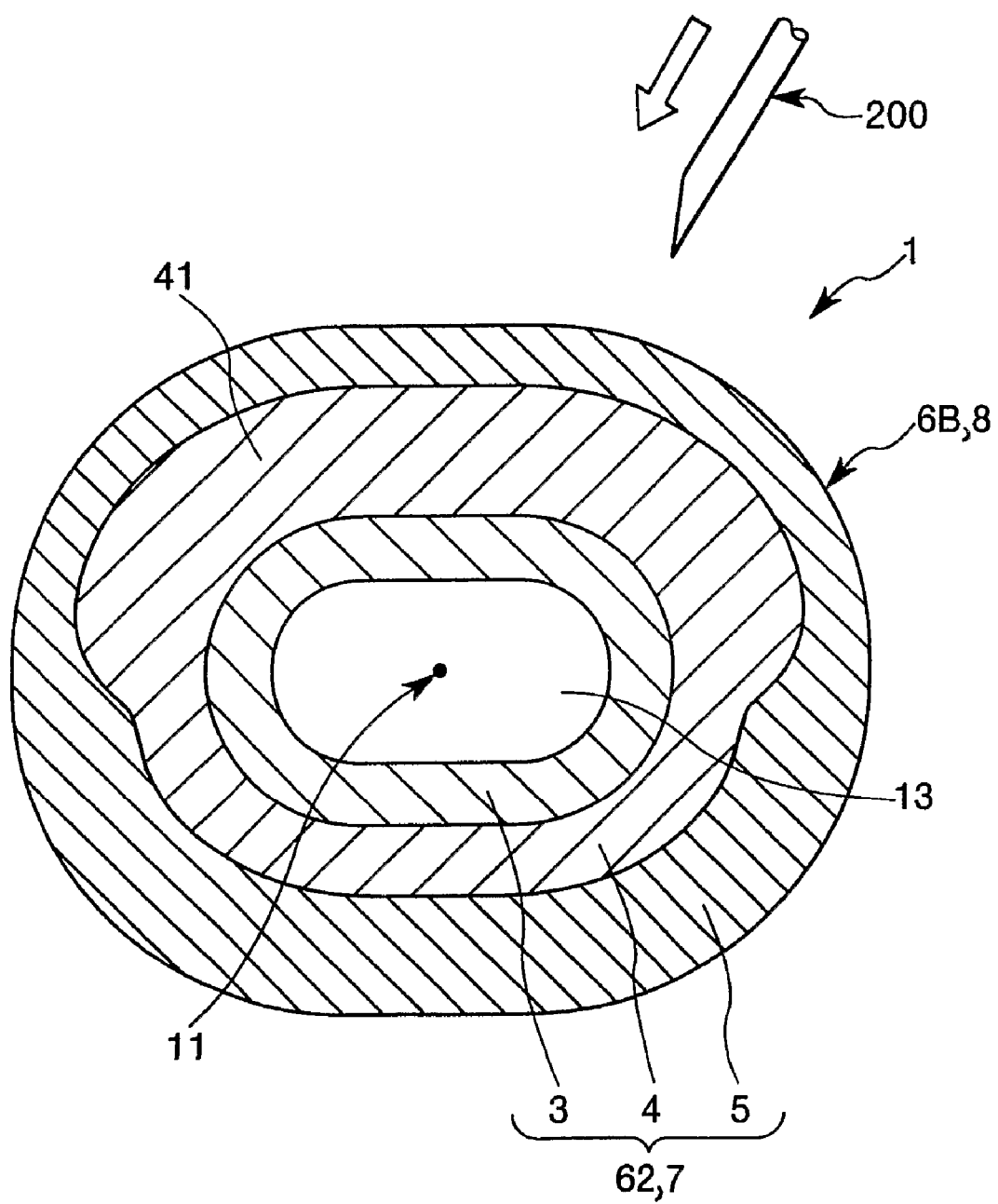
FIG. 6 is a transverse cross-sectional view of a main section of an artificial blood vessel according to a fourth embodiment of the present invention.

FIG. 6 shows in transverse cross-section a main section of an artificial blood vessel according to a fourth embodiment of the present invention. Terms related to vertical directions, such as "upper" and "lower", refer to the orientation of the vessel shown in FIG. 6. In FIG. 6, the vessel wall of the artificial blood vessel is shown with an exaggerated thickness compared with the outside diameter of the artificial blood vessel.

Those features of the artificial blood vessel according to the fourth embodiment, which are different from the artificial blood vessel according to the above embodiments, will mainly be described below, and other common features will not be described below.

The artificial blood vessel according to the fourth embodiment is essentially identical to the artificial blood vessel according to the third embodiment except that the main section has a different transverse cross-sectional shape.

As shown in FIG. 6, a main section 6B has a substantially oval-shaped, i.e. an elliptical, transverse cross-sectional shape. The main section 6B with such a transverse cross-sectional shape is effective to prevent the artificial blood vessel 1 from turning about the central axis 11. Therefore, the artificial blood vessel 1 can be placed in the living body such that the upper intermediate layer 41 is positioned in alignment with the direction in which the artificial blood vessel 1 is pierced with the needle 200, i.e. the upper side in FIG. 6.

Furthermore, since the transverse cross-sectional shape of the main section 6B is oval and the blood passageway 13 defined in the artificial blood vessel 1 remains unchanged, the puncture region 8 has an increased surface area to provide more locations that can be pierced with the needle 200.

Fifth Embodiment

Figure 7:
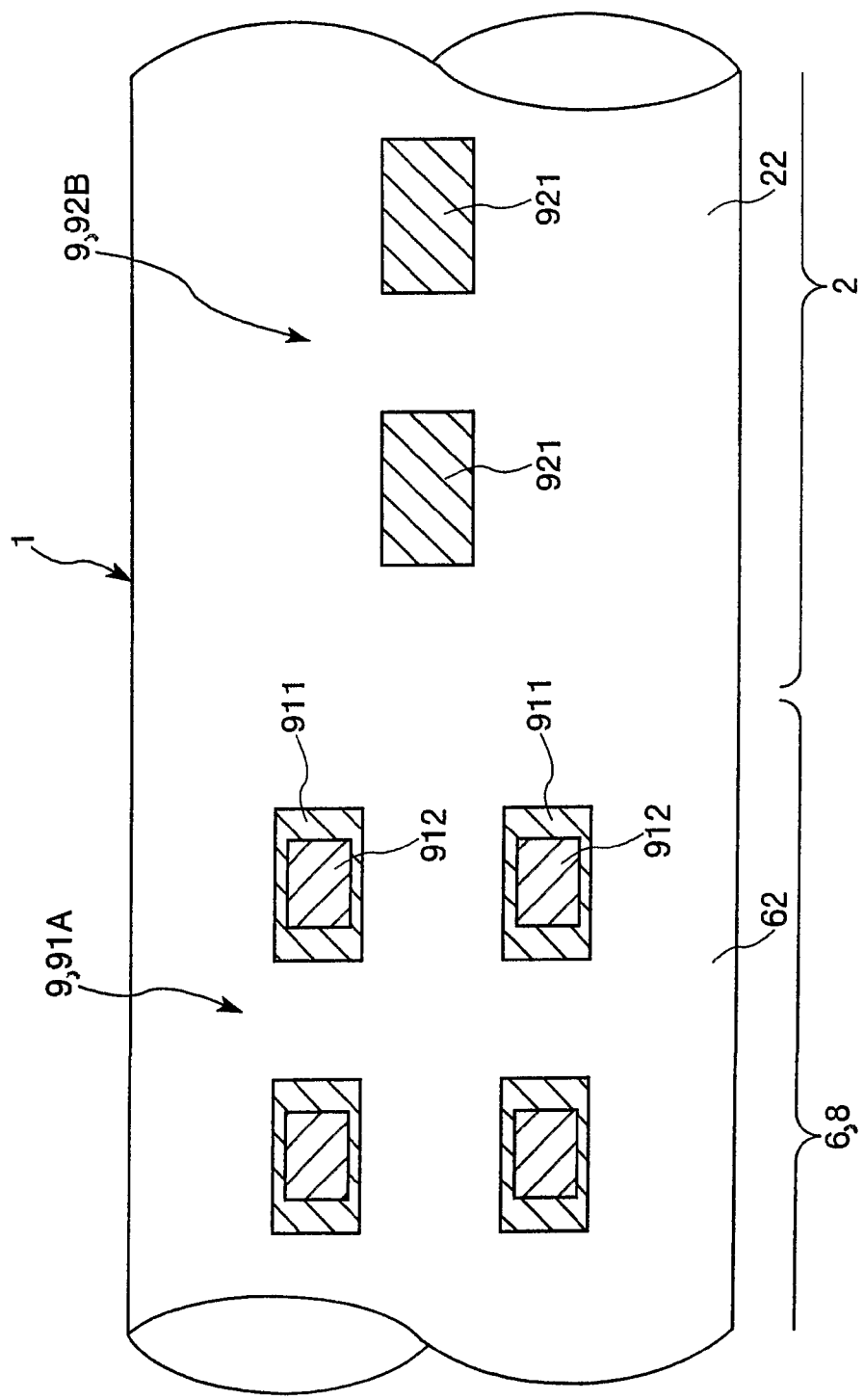
FIG. 7 is an enlarged fragmentary view showing markers of an artificial blood vessel according to a fifth embodiment of the present invention.

FIG. 7 shows in fragment and at an enlarged scale, the markers of an artificial blood vessel according to a fifth embodiment of the present invention.

Those features of the artificial blood vessel according to the fifth embodiment, which are different from the artificial blood vessel according to the above embodiments, will mainly be described below, and other common features will not be described below.

The artificial blood vessel according to the fifth embodiment is essentially identical to the artificial blood vessel according to the first embodiment except that markers have a different arrangement.

As shown in FIG. 7, the main section marker 91A includes first markers 911 used when the artificial blood vessel 1 is embedded into the living body, as with the main section marker 91 according to the first embodiment, and second markers 912 after the artificial blood vessel 1 is embedded into the living body.

Each of the first markers 911 is of an elongate rectangular shape, and is colored for increased visibility. When the artificial blood vessel 1 is embedded into the living body, the first markers 911 give a reliable visual indication of the extent of the puncture region 8.

Each of the second markers 912 is of a rectangular shape, and is positioned within one of the first markers 911. The second markers 912 are not limited to any particular materials, but may for convenience be made of an X-ray contrast material. Even after the artificial blood vessel 1 is embedded into the living body, the second markers 912 allow the extent of the puncture region 8 to be reliably recognized when the second markers 912 are appropriately processed.

An anastomotic section marker 92B comprises first markers 921 used when the artificial blood vessel 1 is embedded into the living body, as with the anastomotic section markers 92 according to the first embodiment. The first markers 921 may be identical in nature to the first markers 911 of the main section marker 91A.

The artificial blood vessels according to the preferred embodiments of the present invention have been described in detail above. However, the principles of the present invention are not limited to the illustrated embodiments. Various parts of the artificial blood vessels may be replaced with desired components capable of performing the same functions as those parts, and desired structural members may be added to the artificial blood vessels.

For example, the transverse cross-sectional shape of the intermediate layer of the main section according to the second embodiment may be replaced with the transverse cross-sectional shape of the intermediate layer of the main section according to the third embodiment. As the artificial blood vessel according to the second embodiment is U-shaped in its entirety, the artificial blood vessel can be placed in the living body such that the upper intermediate layer is reliably positioned in alignment with the direction in which the artificial blood vessel is pierced with the needle.

Furthermore, the transverse cross-sectional shape of the main section according to the second embodiment may be replaced with the transverse cross-sectional shape of the main section according to the fourth embodiment.

The anastomotic section is not limited to being provided on each of the opposite ends of the main section, but may be provided on one of the opposite ends of the main section.

Both the inner layer 3 and the outer layer 5 are not limited to being made of a material including fluoroplastic as a chief material, but either one of the inner layer 3 and the outer layer 5 may be made of a material including fluoroplastics as a chief material, for example.

The markers are not limited to visual markers, but may be touch markers that are recognizable by palpation.

Although certain preferred embodiments of the present invention have been shown and described in detail, it should be understood that various changes and modifications may be made therein without departing from the scope of the appended claims.

The invention claimed is:

1. An artificial blood vessel for use in a region of a living body which needs to be repeatedly pierced with a needle, said vessel comprising:
   a main section having a vessel wall which includes a laminated assembly comprising an inner layer, an outer layer, and an intermediate layer of a self-closable elastic material positioned therebetween; and an anastomotic section comprising an inner layer, an outer layer, and an intermediate layer of a self-closable elastic material positioned therebetween, disposed on each or one of opposite ends of said main section;

wherein the intermediate layer of said anastomotic section is thinner than the intermediate layer of said main section, so that said anastomotic section has a vessel wall thinner than said main section.

2. An artificial blood vessel according to claim 1, wherein said intermediate layer of said anastomotic section has a thickness in the range from 10 to 90% of the thickness of the intermediate layer of said main section.

3. An artificial blood vessel according to claim 1, wherein said anastomotic section has an outside diameter smaller than the outside diameter of said main section.

4. An artificial blood vessel according to claim 1, wherein said intermediate layer comprises a thermoplastic elastomer.

5. An artificial blood vessel according to claim 1, wherein at least one of said inner layer or said outer layer comprises a fluoroplastic material.

6. An artificial blood vessel according to claim 1, further comprising:

markers for distinguishing said main section and said anastomotic section from each other.

7. An artificial blood vessel according to claim 6, wherein said markers are disposed respectively on said main section and on said anastomotic section, and are different from each other.

8. An artificial blood vessel according to either one of claims 6 and 7, wherein said markers are used when the artificial blood vessel is embedded into a living body.

9. An artificial blood vessel according to either one of claims 6 and 7 wherein said markers are used after the artificial blood vessel is embedded into a living body.

10. An artificial blood vessel according to claim 1, wherein said artificial blood vessel is entirely in the shape of an I in its natural state.

11. An artificial blood vessel according to claim 1, wherein said artificial blood vessel is entirely in the shape of a U in its natural state.

12. An artificial blood vessel according to claim 1, including a U-shaped curved portion disposed on said main section.

13. An artificial blood vessel according to claim 1, wherein said intermediate layer of said main section has a portion having a thickness different from the thickness of another portion thereof.

14. An artificial blood vessel according to claim 1, wherein said main section has an essentially elliptical transverse cross-sectional shape.

15. A method of accessing the vasculature of a patient in need thereof, said method comprising:

a) implanting an artificial blood vessel as claimed in claim 1 as an arterial-venous shunt interconnecting an artery and a vein of the patient; and b) puncturing the main section of the artificial blood vessel with a needle to access the vasculature of the patient;

wherein the puncture of the main section of the vessel wall by the needle is closed by the intermediate layer following withdrawal of the needle.

\* \* \* \* \*